(12) United States Patent
Quinn et al.

(10) Patent No.: US 7,497,839 B2
(45) Date of Patent: Mar. 3, 2009

(54) ANKLE SUPPORT

(75) Inventors: Patrick J. Quinn, Eagan, MN (US);
Frank W. Campbell, Lake Elmo, MN (US)

(73) Assignee: Swede-O, Inc., North Branch, MN (US)

( * ) Notice: Subject to any disclaimer, the term of this patent is extended or adjusted under 35 U.S.C. 154(b) by 229 days.

(21) Appl. No.: 11/215,323

(22) Filed: Aug. 29, 2005

(65) Prior Publication Data

US 2007/0049857 A1 Mar. 1, 2007

(51) Int. Cl.
*A61F 5/00* (2006.01)
(52) U.S. Cl. .......................................... 602/23; 602/27
(58) Field of Classification Search ............. 602/23–29, 602/60–64, 65, 5; 128/882
See application file for complete search history.

(56) References Cited

U.S. PATENT DOCUMENTS

| | | | |
|---|---|---|---|
| 1,374,669 A | 4/1921 | McClellan | |
| 2,450,862 A | 10/1948 | Wilkinson | |
| 3,327,410 A | 6/1967 | Park, Sr. et al. | |
| 3,613,273 A | 10/1971 | Marquis | |
| 3,674,023 A | 7/1972 | Mann | |
| 3,970,083 A | 7/1976 | Carrigan | |
| 4,133,311 A | 1/1979 | Karczewski | |
| 4,323,058 A | 4/1982 | Detty | |
| 4,527,556 A | 7/1985 | Nelson | |
| 4,869,267 A | 9/1989 | Grim et al. | |
| 4,878,504 A | 11/1989 | Nelson | |
| 5,067,486 A | 11/1991 | Hely | |
| 5,217,431 A | 6/1993 | Toronto et al. | |
| 5,445,598 A | 8/1995 | Nguyen-Senderowicz | |
| 5,676,641 A * | 10/1997 | Arensdorf et al. | 602/27 |
| 5,795,316 A * | 8/1998 | Gaylord | 602/27 |
| 5,891,073 A * | 4/1999 | Deirmendjian et al. | 602/27 |
| 5,899,872 A | 5/1999 | Gilmour | |
| 6,117,098 A * | 9/2000 | Weber et al. | 602/27 |
| 6,398,750 B1 | 6/2002 | Quinn et al. | |
| 6,652,474 B1 | 11/2003 | Quinn et al. | |
| 6,663,583 B1 | 12/2003 | Janis | |
| 2005/0033216 A1 | 2/2005 | Campbell | |

* cited by examiner

*Primary Examiner*—Michael A. Brown
(74) *Attorney, Agent, or Firm*—IPLM Group, P.A.

(57) ABSTRACT

An ankle brace utilizes first and second strap segments. The strap segments are positioned proximate the bottom portion of the brace and extends up and across the front portion of the brace before being secured about the brace.

22 Claims, 14 Drawing Sheets

ANKLE SUPPORT

BACKGROUND OF THE INVENTION

1. Field of the Invention

This invention relates generally to an ankle brace and more particularly to an ankle brace having strap segments that each are positioned underneath a user's foot and then are wrapped over a user's foot and around.

2. Description of the Prior Art

The human ankle consists of three bones, the tibia, the fibula, and the talus, which are bound to the bones of the foot and to one another by ligaments. The particular arrangement of the three bones allows the foot to rotate about three orthogonal axes relative to the leg. The ligaments place elastic limits on the extent of such rotation or movement.

Many ankle injuries occur when ankle movement exceeds the elastic limit of one or more ligaments. One relatively common ankle injury, known as eversion of the ankle, results when the ankle moves too far outward as the foot rolls over. Another relatively common ankle injury, known as inversion of the ankle, results when the ankle moves too far inward as the foot rolls over. Many individuals, and athletes in particular, require external support for their ankles as a result of previous eversion or inversion injuries or ongoing concerns about adequately protecting their ankles.

A common practice among athletes is to tightly wrap the ankles with medical adhesive tape. Although "taping" is generally recognized as an effective way to protect a weak or injured ankle, it suffers several drawbacks, as well. For example, an effective tape job necessarily restricts movement of the foot in all directions relative to the leg, thereby limiting desirable ankle motions as well as undesirable ones. Taping is also relatively costly because the tape is typically used only once, and it often requires a trainer to be properly applied.

Fabric ankle wraps are sometimes used as an alternative to taping. The fabric wraps may be used more than once, but their elasticity and lack of adhesiveness renders them less effective than medical tape in terms of immobilizing the joint.

A variety of relatively rigid support structures have been designed as alternatives to medical tape and fabric wraps. However, those skilled in the art continue to seek improvements in areas such as reliable support, user comfort, user mobility, application simplicity, and/or manufacturing cost.

SUMMARY OF THE INVENTION

In one embodiment, the invention is an ankle brace for use in supporting an ankle bone and ankle joint. The brace includes a body adapted and configured to embrace a user's ankle. The body has a bottom portion for being positioned under a user's foot, a front portion, a back portion, a first side and a second side. A first strap segment has a first region positioned proximate the bottom portion of the body, a second region extending up the first side of the body and across the front portion and a third region secured to the body. A second strap segment has a first region positioned proximate the bottom portion of the body, a second region extending up the second side of the body and across the front portion, crossing the second region of the first strap segment, and a third region extending around the back of the body.

In another embodiment, the invention is an ankle brace for use in supporting an ankle bone and joint. The brace has a body adapted and configured to embrace a user's ankle. The body has a bottom portion for being positioned under a user's foot, a front portion, a back portion, a first side and second side. A first strap segment has a first end, a second end and an intermediate region between the first end and the second end. The second end of the first strap segment is secured to the body and the intermediate region of the first strap segment is adapted and configured for supporting the ankle bone and joint. A second strap segment has a first end, a second end and an intermediate region between the first end and the second end. The intermediate region of the second strap segment is adapted and configured for supporting the ankle bone and joint and also for being wrapped around a user and overlap itself and the first strap segment. The second end of the second strap segment is secured to the body, wherein the second end of the second strap segment further secures both the first and second strap segments around the user.

In another embodiment, the invention is a method of wrapping first and second strap segments of an ankle brace around an ankle bone and ankle joint. The method includes wrapping a first strap segment underneath a bottom portion of a brace before going across a front portion. The first strap segment is then secured to the brace. The second strap segment is then brought up from the bottom portion before going across the front portion and the second strap segment is brought across the front portion of the brace. The second strap segment is then secured about the brace.

DETAILED DESCRIPTION OF A PREFERRED EMBODIMENT

Figure 1:
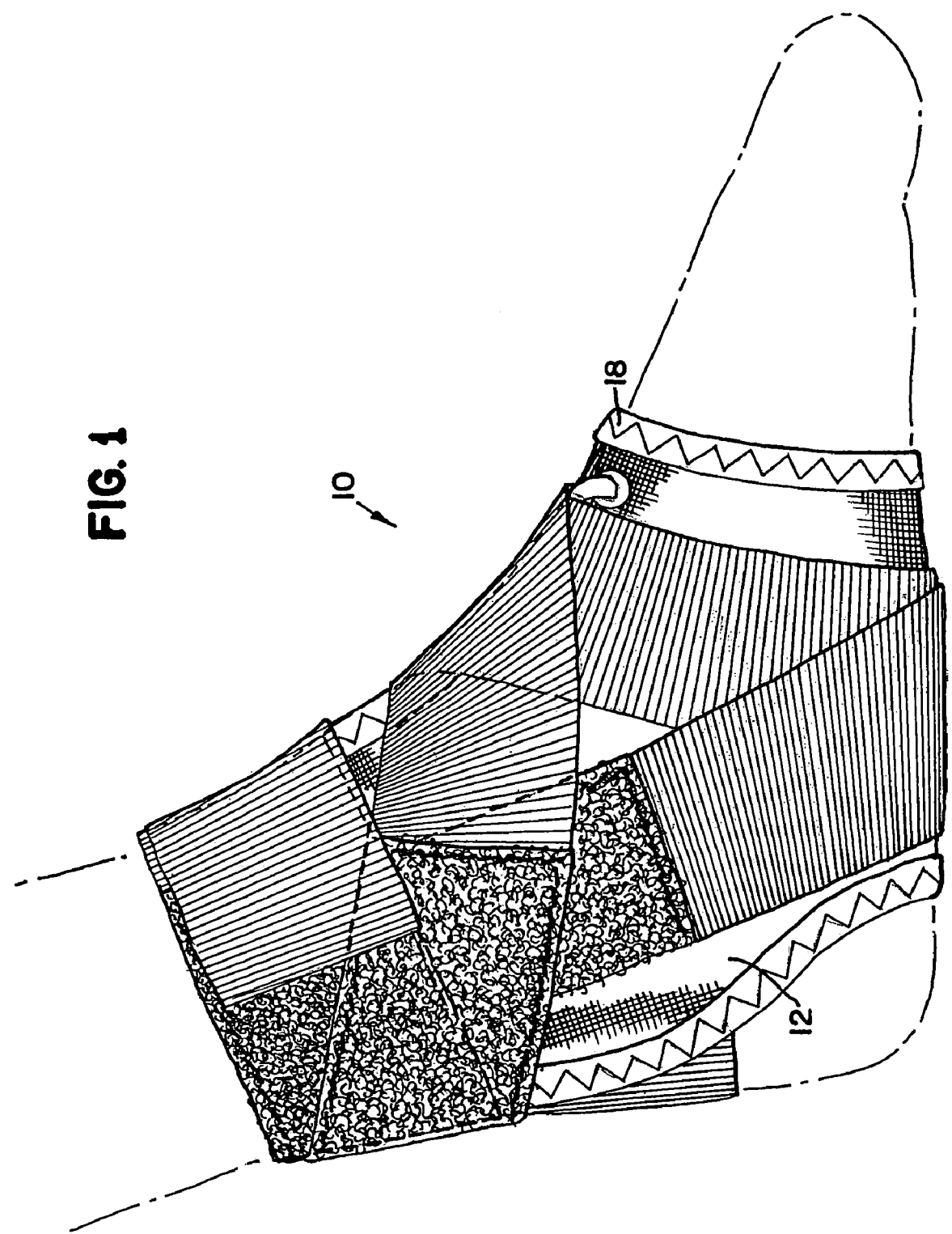
FIG. 1 is a side elevational view of the ankle support constructed according to the principles of the present invention.
Figure 2:
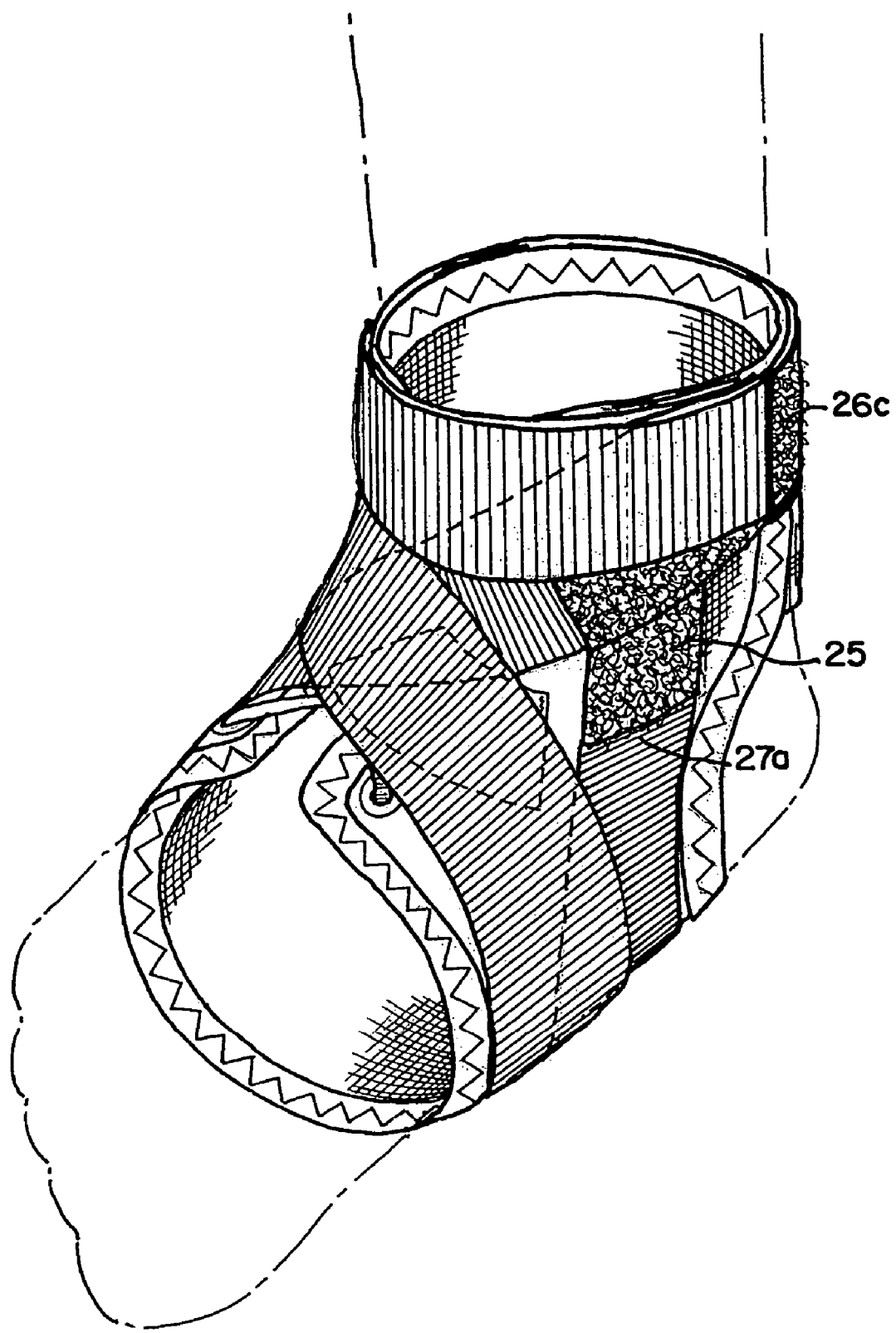
FIG. 2 is a perspective view of the ankle brace, shown in FIG. 1, taken generally from the opposite side as shown in FIG. 1.
Figure 3:
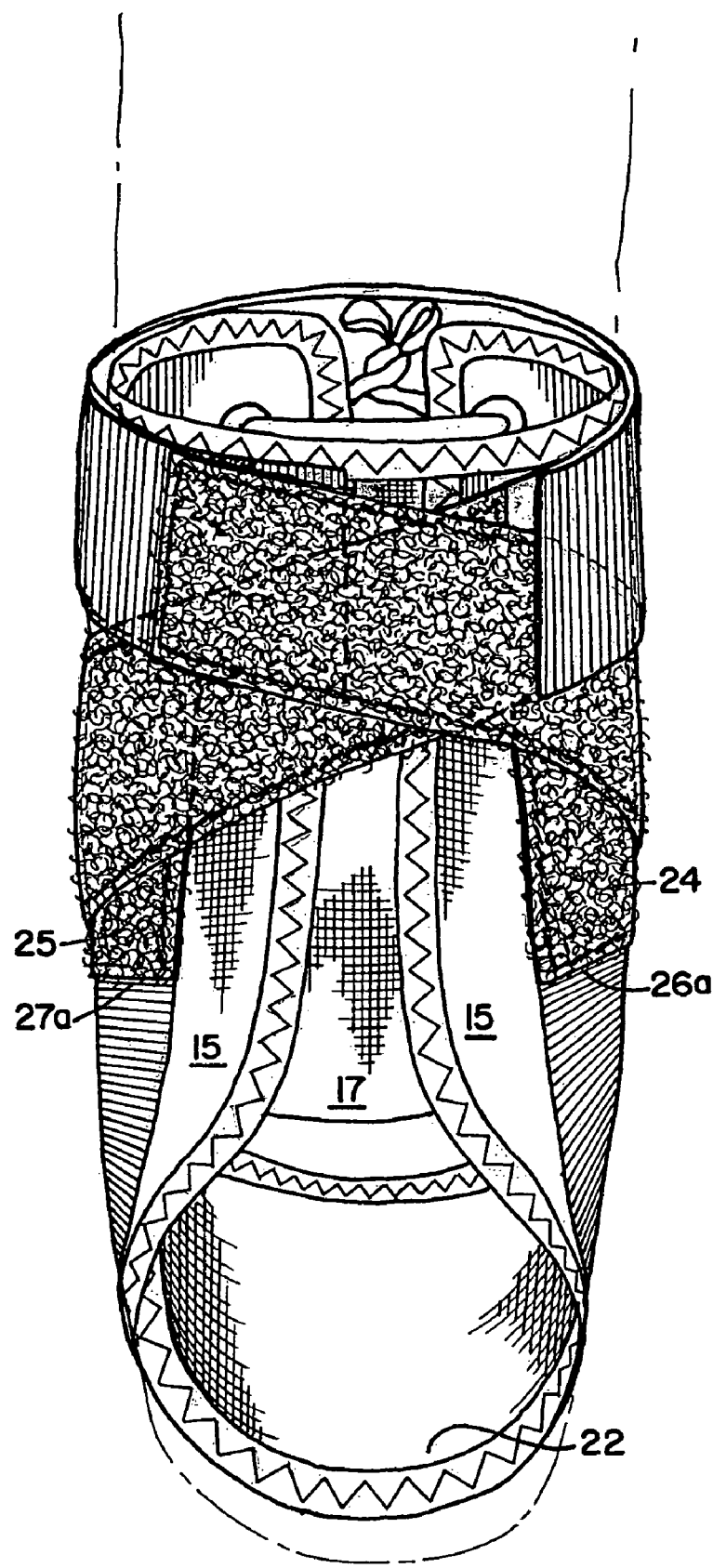
FIG. 3 is a rear elevational view of the brace shown in FIG. 1.

Referring to the drawings, wherein like numerals represent like parts throughout the several views, there is generally disclosed at 10 an ankle support or brace. The ankle brace 10 includes a first portion 11 that forms a boot-like member which encircles the ankle to be supported. The boot-like member 11 is a body that is adapted and configured to embrace a user's ankle. The first portion 11 has a right side 12, a left side 13, a bottom portion 14, a back portion 15, and a front portion 16. The front portion 16 is proximate both the right side 12 and left side 13. The first portion 11, thus far described, is preferably formed from a one-piece material. The right side 12 is operatively connected to the left side 13 at the front by stretchable mesh tongue 17. The mesh tongue 17 is connected to the first portion 11 by suitable means such as stitching. The rear portions of the right side 12 and left side 13 are connected by an elastic member 17 by suitable means such as stitching. The elastic member 17 provides for some expansion between the spaced-apart back edges of the right side 12 and left side 13. A suitable binding 18 is secured around the periphery of the first portion 11. The binding 18 may be of any suitable material such as a polyester binding tape. A plurality of openings 19 are formed along the front portions of the right side 12 and left side 13. Eyelets 20 are secured to the openings 19. The first portion 11 forms three openings. The first opening 21 is positioned proximate the toes of the user. The second opening 22 is the heel opening. The third opening 23 is formed at the top of the first portion 11 and is formed for the lower part of the leg of the user proximate the ankle. A first strip of hook material 24 is operatively connected by suitable means, such as stitching, to the right side 12 and extends vertically from proximate the top of the first portion 11 to midway down the first portion 11. Similarly, a second strip of hook material 25 is operatively connected to the left side 13 and again extends vertically from proximate the top of the first portion 11 to midway down the left side 13. Throughout this application, a suitable hook-and-loop material such as Velcro® material may be utilized. Further, it is understood that one section of hook material mates with one section of loop material, the materials may be interchanged, as long as there is one of each type.

The ankle brace 10 includes a first strap segment 26 and a second strap segment 27. The strap segments 26, 27 are wrapped around the first portion 11, as will be more fully described hereinafter, to support an ankle bone and ankle joint. The second strap segment 27 has a first end 27a that is operatively connected to the left side 13 by suitable means such as stitching. A second end 27b is free to be wrapped around the user, as will be described more fully hereafter. Further, the second strap segment 27 has a first region 31 that is positioned proximate the bottom portion of the body or first portion 11. A second region 32 extends up the right side 12 of the body 11 and across the front portion 16. A third region 33 (proximate the second end 27b) is secured to the first portion 11. A strip of hook material 27c is secured to the outside of the second strap segment 27 and a strip of loop material 27d is secured to the inside of the strap segment 27 proximate the second end 27b. This allows for the strap segment 27 to be wrapped around the user's ankle and then secured back on itself by having the hook material 27d mate with the loop material 27c. While it is preferable that the strap segment 27 extends around the ankle of the user and loop back onto itself, it is understood that it would not be necessary to extend and circle ankle and may be terminated after it has crossed the front portion 16. It would still be secured to the body 11 after crossing across the front portion 16. However, by encircling the user's ankle, as shown in the figures, the strap segment 27 is more fully secured around the ankle.

The first strap segment 26 has a first end 26a that is operatively connected to the right side 12 by suitable means such as stitching. A second end 26b is free to be wrapped around the user, as will be described more fully hereafter. Further, the first strap segment 26 has a first region 28 that is positioned proximate the bottom portion of the body or first portion 11. A second region 29 extends up the left side 13 of the body 11 and across the front portion 16. A third region 30 is secured to the first portion 11. A strip of hook material 26c is secured to the outside of the first strap segment 26 and a strip of loop material 26d is secured to the inside of the strap segment 26 proximate the second end 26b. This allows for the strap segment 26 to be wrapped around the user's ankle and then secured back on itself by having the hook material 26c mate with the loop material 26d.

Figure 6:
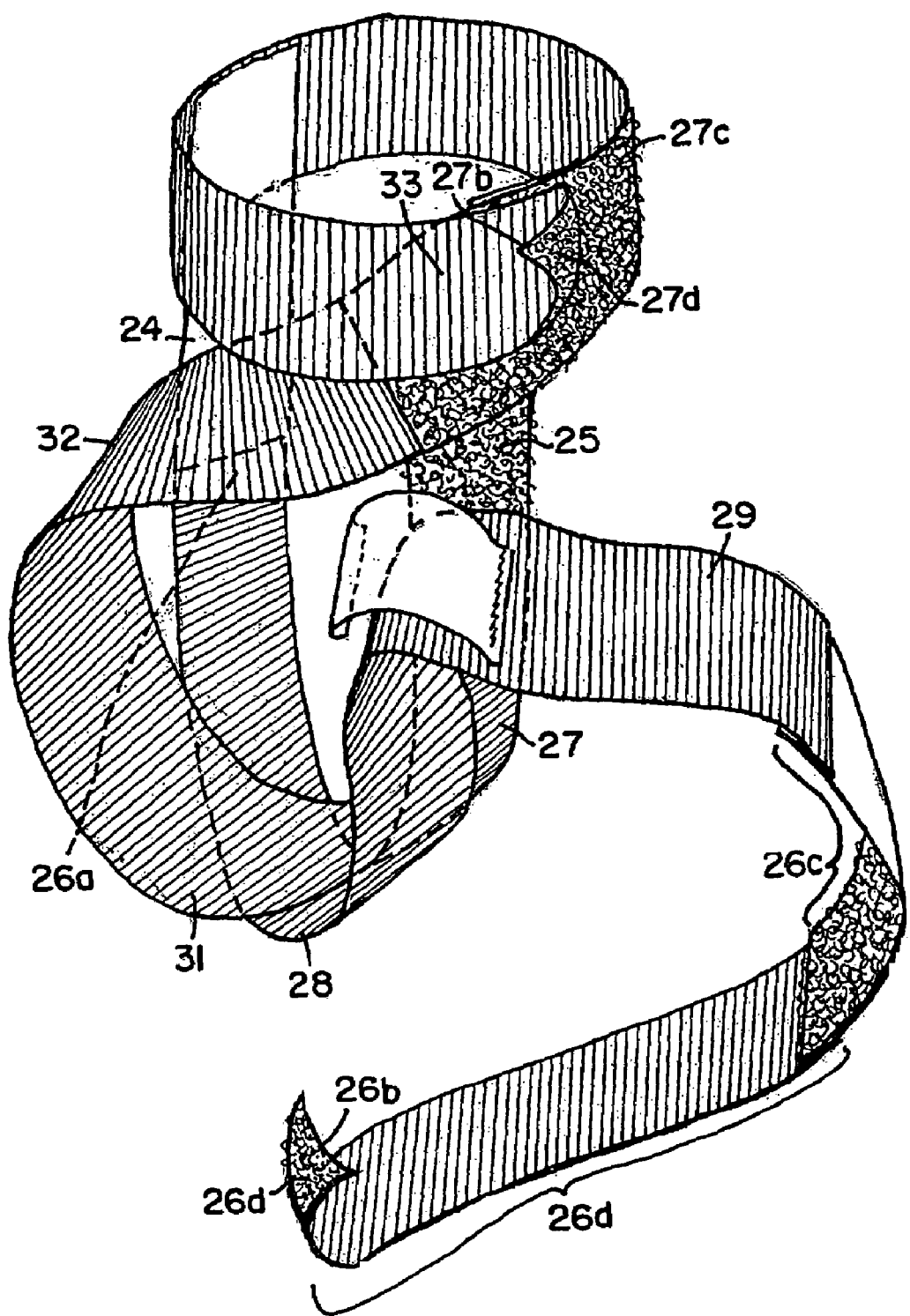
FIG. 6 is a perspective view of the strap segments shown in FIG. 5, with one of the strap segments unwrapped.
Figure 7:
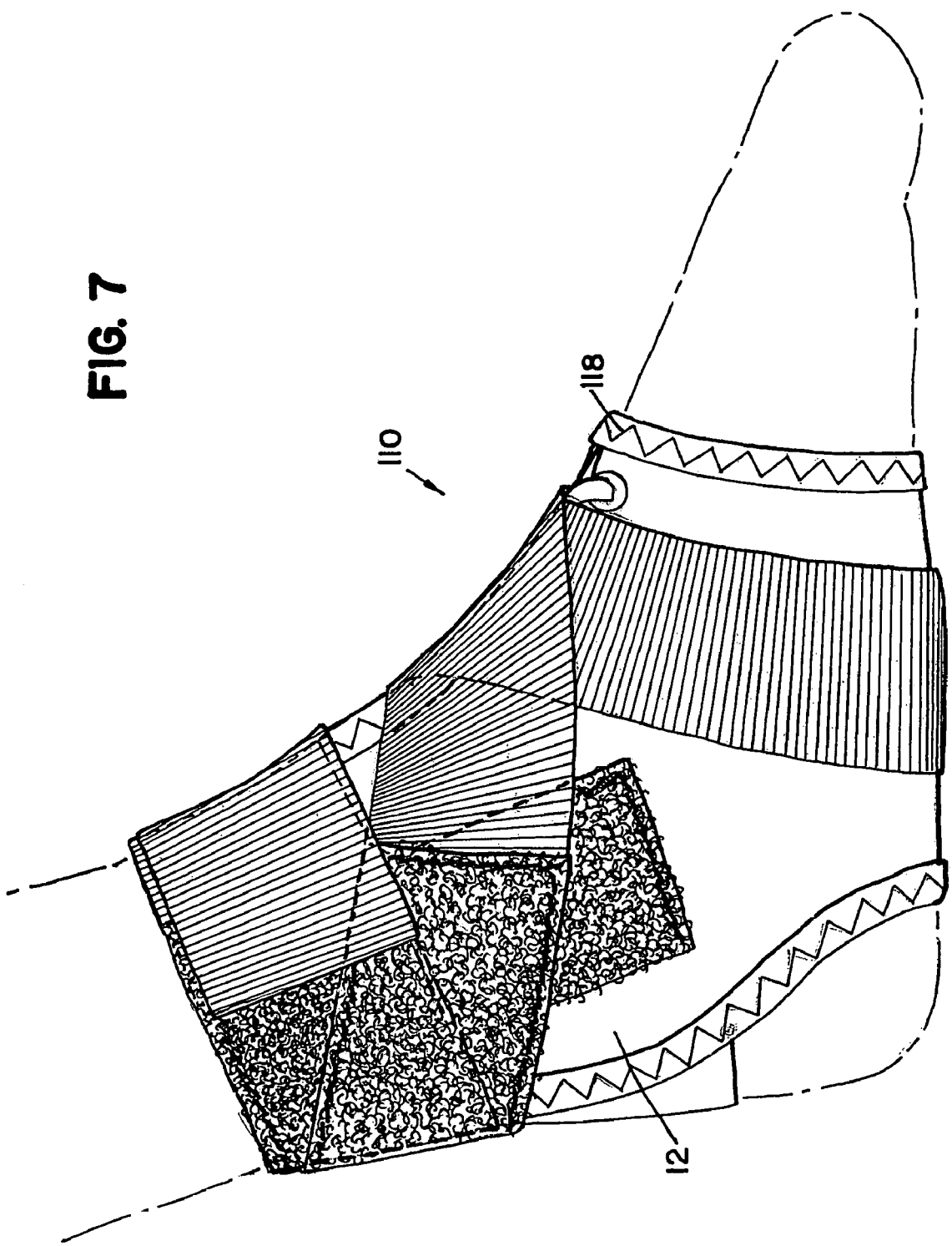
FIG. 7 is a side elevational view of a second embodiment of an ankle brace made in accordance with the principles of the present invention.
Figure 8:
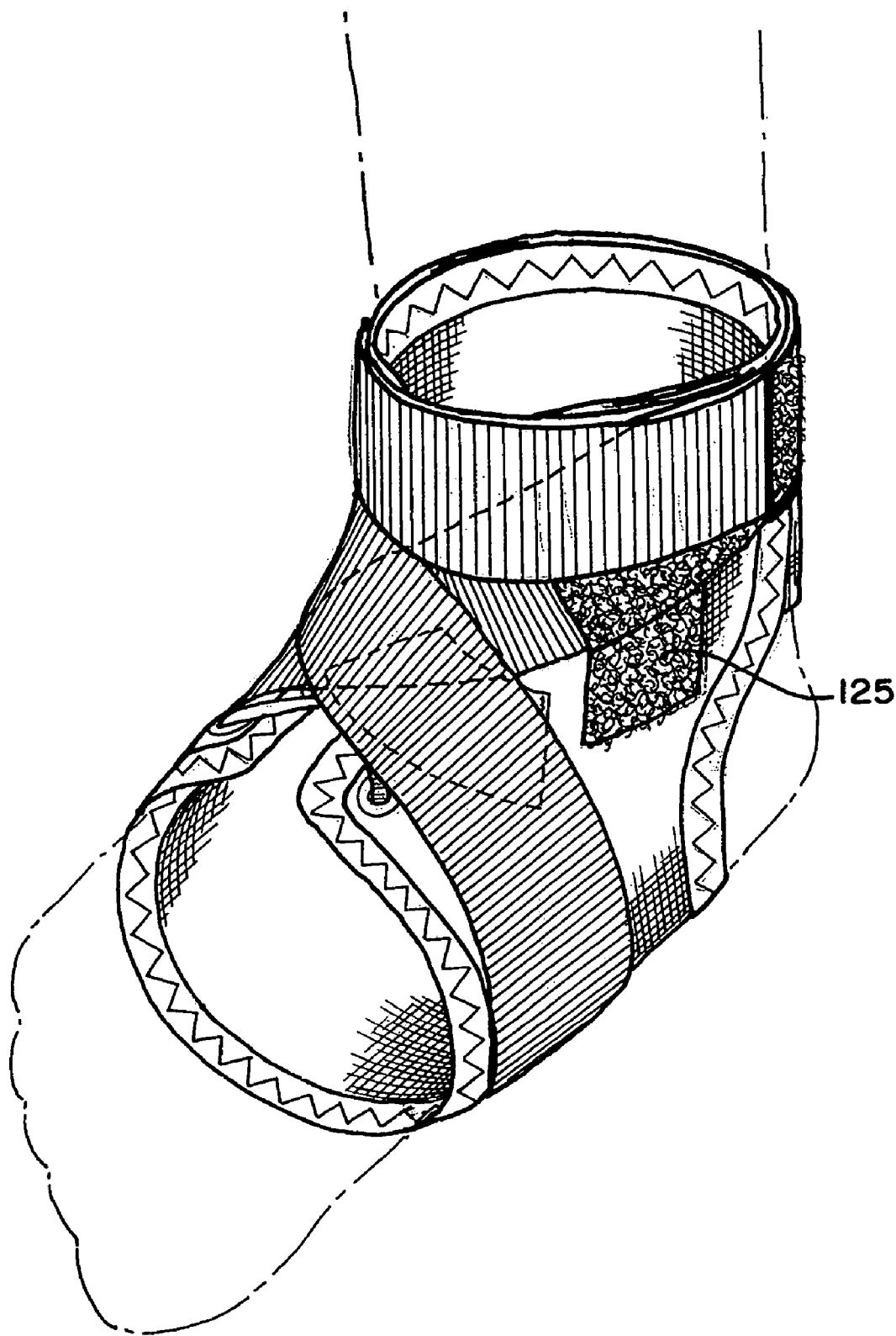
FIG. 8 is a perspective view of the ankle brace shown in FIG. 7, shown generally from the opposite side.
Figure 9:
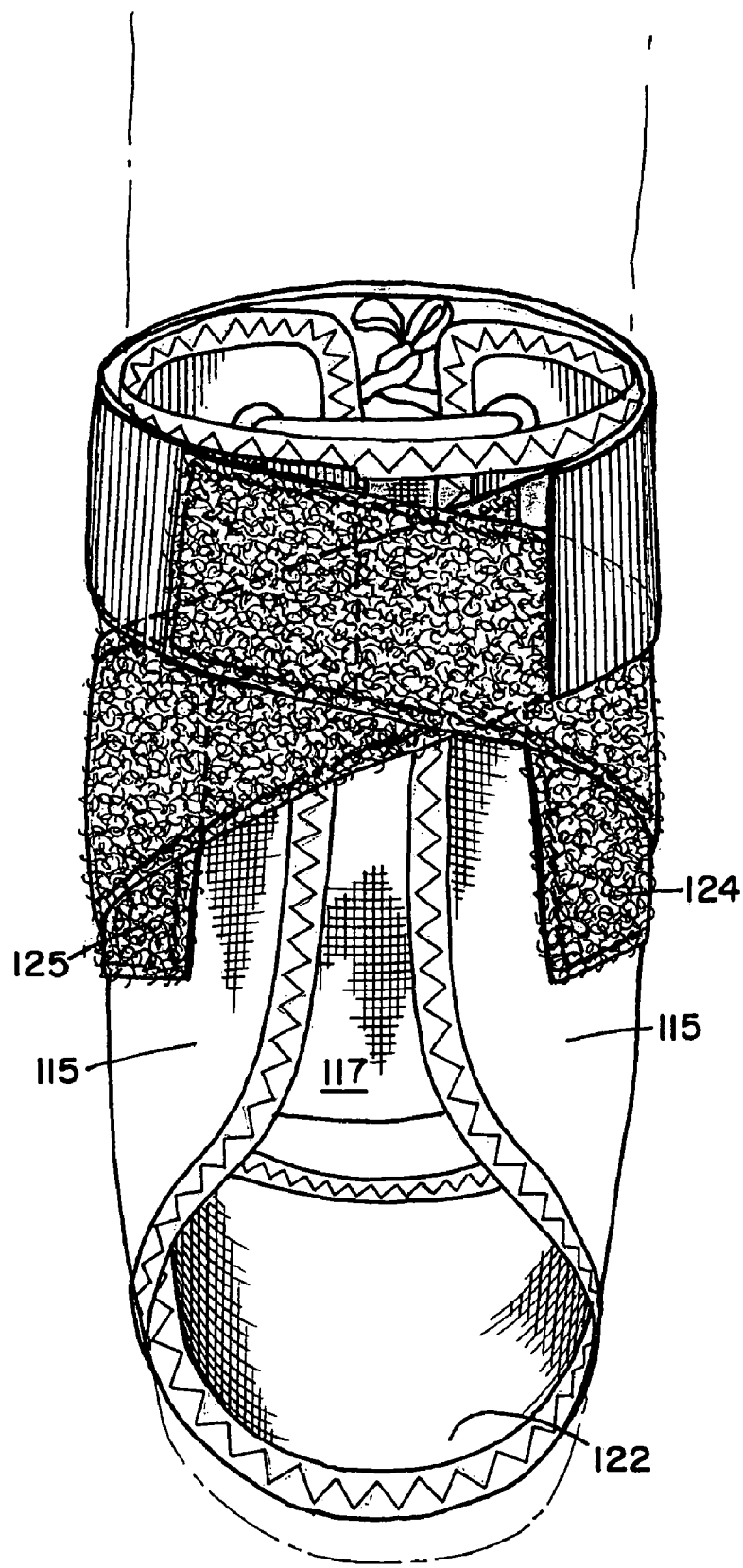
FIG. 9 is a rear elevational view of the ankle brace shown in FIG. 7.

In viewing FIG. 6, the layout of the hook material 26d and the loop material 26c can be seen. The loop material 26d is on the inside of the strap 26 and is approximately four inches in length. The loop material 26c is on the outside of the strap and extends for a distance of approximately five to six inches. It is of course understood that other suitable lengths may be utilized and may very well be dependent upon the size of the ankle brace. The hook material 27d and loop material 27c are similarly located on strap segment 27.

The strap segments 26 and 27 may be of any suitable material such as a webbing material that is not stretchable. However, there may be some advantage to having the portion of the strap segments 26, 27 that are proximate the ends 26b and 27b to be made of an elastic material to allow for some minimal stretch of an additional 1-2 inches. This would typically be the portion having the loop material 26d, 27d.

Figure 4:
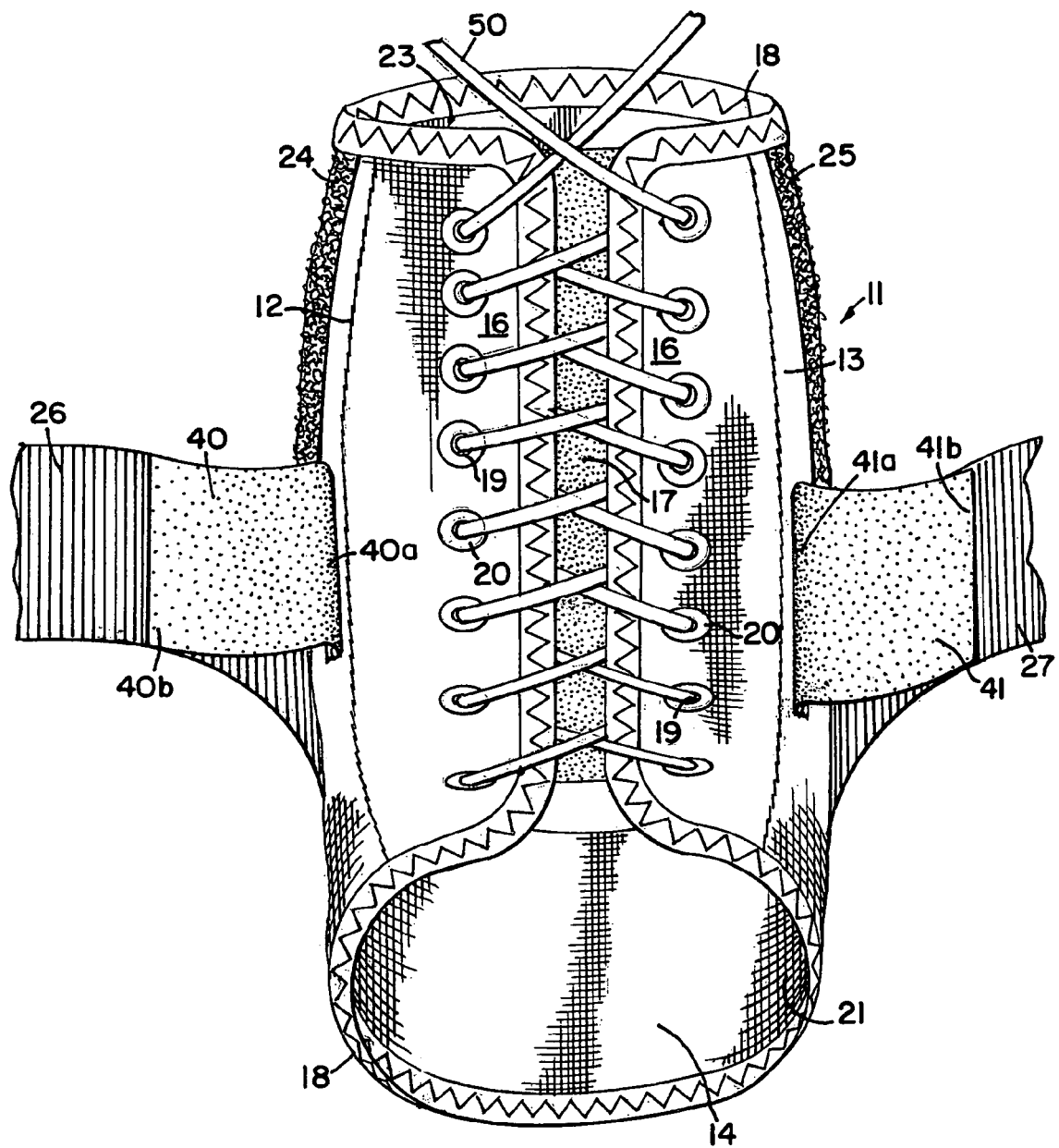
FIG. 4 is a front elevational view of the brace shown in FIG. 1, with the strap segments unwrapped.

As shown in FIG. 4, the ankle brace 10 has two prepositioning members 40, 41. The prepositioning members 40, 41 have a first end 40a, 41a that is secured to the first portion 11 by suitable means such as stitching. A second end 40b, 41b is secured to the strap segments 26, 27. The prepositioning members 40, 41 assist in keeping the strap segments 26, 27 in proper orientation as the user is putting on the ankle brace 10. The prepositioning members 40, 41 may have some stretch.

Figure 5:
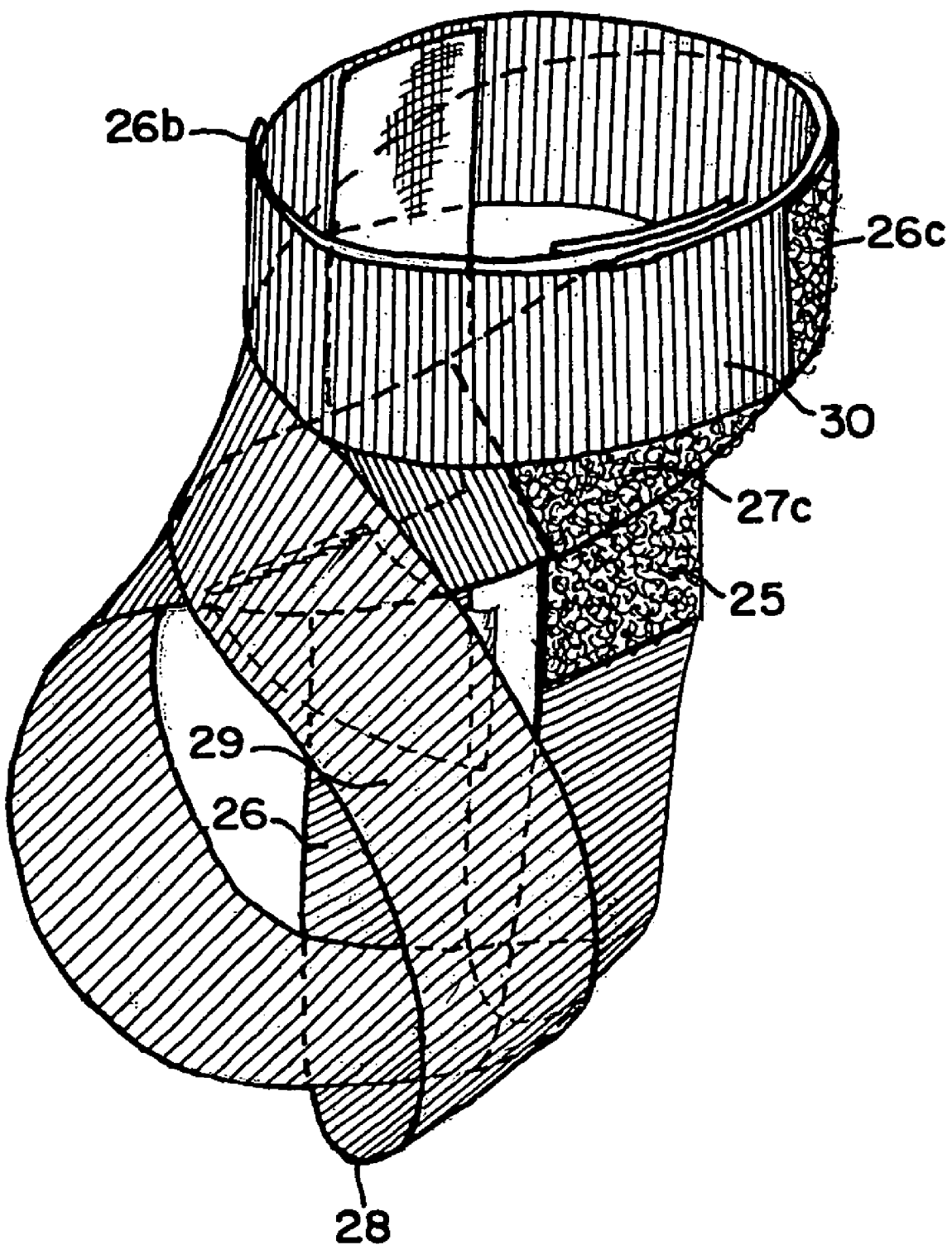
FIG. 5 is a perspective view of the strap segments of the ankle brace shown in FIG. 2.

In use, the ankle brace 10 is placed on the user's foot and the laces 50 are tightened. Then, either one of the strap segments 26 or 27 are tightened first. The following discussion will have the second strap segment 27 being secured first, although it is recognized that the first strap segment 26 could also be secured first. FIG. 6 shows the ankle brace 10 with the second strap segment 27 secured first. The second strap segment 27 extends down from the hook material 25 and the first region 31 is positioned proximate underneath the bottom portion 14 of the first portion 11. Then, the second region 32 of the strap 27 is brought up the right side 12 and across the front portion 16 and the third region 33 is wrapped around the user's ankle and the second end 27b is secured by use of the loop material 27d being secured to the hook material 27c. As previously discussed, it would not be necessary that the strap segment 27 be so long as to encircle the ankle of the user. It would be possible to have the second end 27b terminate earlier and be connected to the body at another point such as proximate the hook material 25. If that is the case, the loop material 27d could be secured to the hook material 25, thereby securing the second strap. However, as previously stated, it is preferable that the second strap segment 27 extends around and encircles the ankle. Then, the first strap segment 26 is secured. This is shown completed in FIG. 5. The first region 28 is positioned under the bottom portion 14 of the first portion 11. Then, the second region 29 extends up the left side 13 and across the front portion 16. The second region 29 extends across a portion of the second region 32 of the second strap segment 27. The second end 26b is wrapped around the back of the body 11 so that the third region 33 encircles the user's ankle. The strap 26 is secured to itself and therefore also secured about the first portion 11 by means of the hook material 26c mating with the loop material 26d at the second end 26b. The first strap segment 26 also overlaps the second strap 27 at the third region 33 and therefore not only secures itself (strap segment 26) to the first portion 11 but also further secures the second strap segment 27 to the first portion 11. While it has been described that the strap segment 26 is secured to the body 11, it is understood that there is no direct connection. The tightening, wrapping and securing to itself results in securing the second strap to the body 11, even though there is no direct connection. The strap segments 26 and 27 have a unique wrapping in that they both extend underneath the foot portion before crossing across the front portion 16. The prior art braces have their straps cross the front portion and then go under the foot during the wrapping process.

Referring now to FIGS. 7 through 12, there is shown a second embodiment of an ankle brace 110. The ankle brace 110 includes a first portion 111 that forms a boot-like member which encircles the ankle to be supported. The boot-like member 111 is a body that is adapted and configured to embrace a user's ankle. The first portion 111 has a right side 112, a left side 113, a bottom portion 114, a back portion 115, and a front portion 116. The front portion 116 is proximate both the right side 112 and left side 113. The first portion 111, thus far described, is preferably formed from a one-piece material. The right side 112 is operatively connected to the left side 113 at the front by stretchable mesh tongue 117. The mesh tongue 117 is connected to the first portion 111 by suitable means such as stitching. The rear portions of the right side 112 and left side 113 are connected by an elastic member 117 by suitable means such as stitching. The elastic member 117 provides for some expansion between the spaced-apart back edges of the right side 112 and left side 113. A suitable binding 118 is secured around the periphery of the first portion 111. The binding 118 may be of any suitable material such as a polyester binding tape. A plurality of openings 119 are formed along the front portions of the right side 112 and left side 113. Eyelets 120 are secured to the openings 119. The first portion 111 forms three openings. The first opening 121 is positioned proximate the toes of the user. The second opening 122 is the heel opening. The third opening 123 is formed at the top of the first portion 111 and is formed for the lower part of the leg of the user proximate the ankle. A first strip of hook material 124 is operatively connected by suitable means, such as stitching, to the right side 112 and extends vertically from proximate the top of the first portion 111 to midway down the first portion 111. Similarly, a second strip of hook material 125 is operatively connected to the left side 113 and again extends vertically from proximate the top of the first portion 111 to midway down the left side 113. Throughout this application, a suitable hook-and-loop material such as Velcro® material may be utilized. Further, it is understood that one section of hook material mates with one section of loop material, the materials may be interchanged, as long as there is one of each type. As can be seen, the first portion 111 is identical to the first portion 11 of the ankle brace 10.

The ankle brace 110 includes a first strap segment 126 and a second strap segment 127. While the strap segments 126, 127 will be described in detail hereafter, they do function substantially the same as the strap segments 26, 27. However, the strap segments 126, 127 are continuous and is a single strap, with the two strap segments 126, 127 being operatively connected thereto. In comparing the ankle brace 110 to the ankle brace 10, the portions of the strap segments 26, 27 that extend down from the hook portions 24, 25 have been eliminated and the strap segments operatively connected underneath the bottom portion of the brace. With that as a background, the strap segments 126, 127 will now be described in more detail.

The strap segments 126, 127 are wrapped around a first portion 111, as will be more fully described hereinafter, to support an ankle bone and ankle joint. The second strap segment 127 has a first end 127a that is operatively connected to a first end 126a of the first strap segment 126. Preferably, the ends 127a, 126a are operatively connected by being an integral one-piece strap. However, it is understood that they coutd be sewn together. Further, while not shown, where the ends 127a, 126a meet, stitching may be applied to secure the ends 127a, 126a to first portion 111. This assists in keeping the straps 126, 127 in position. A second end 127b of second strap 127 is free to be wrapped around the user, as will be described more fully hereafter. Further, the second strap segment 127 has a first region 131 that is positioned proximate the bottom portion of the body or first portion 111. A second region 132 extends up the right side 112 of the body 111 and across the front portion 116. A third region 133 (proximate the second end 127b) is secured to the first portion 111. A strip of hook material 127c is secured to the outside of the second strap segment 127 and a strip of loop material 127d is secured to the inside of the strap segment 127 proximate the second end 127b. This allows for the strap segment 127 to be wrapped around the user's ankle and then secured back on itself by having the hook material 127d mate with the loop material 127c. While it is preferable that the strap segment 127 extends around the ankle of the user and loop back on to itself, it is understood that it would not be necessary to extend and circle the ankle and maybe terminated after it crosses the front portion 116. It would still be secured to the body 111 after crossing across the first portion 116. However, by encircling the user's ankle, as further shown in the figures, the strap segment 127 is more fully secured around the ankle.

The first strap segment 126 has a first end 126a and a second end 126b that is free to be wrapped around the user, as will be more fully described hereafter. Further, the first strap segment 126 has a first region 128 that is positioned proximate the bottom portion of the body or first portion 111. A second region 129 extends up the left side 113 of the body 111 and across the front portion 116. A third region 130 is secured about the first portion 111. A strip of hook material 126c is secured to the outside of the first strap segment 126 and a strip of loop material 126d is secured to the inside of the strap segment 126 proximate the second end 126b. This allows for the strap segment 126 to be wrapped around the user's ankle and then secured back on itself by having the hook material 126c mate with the loop material 126d.

Figure 12:
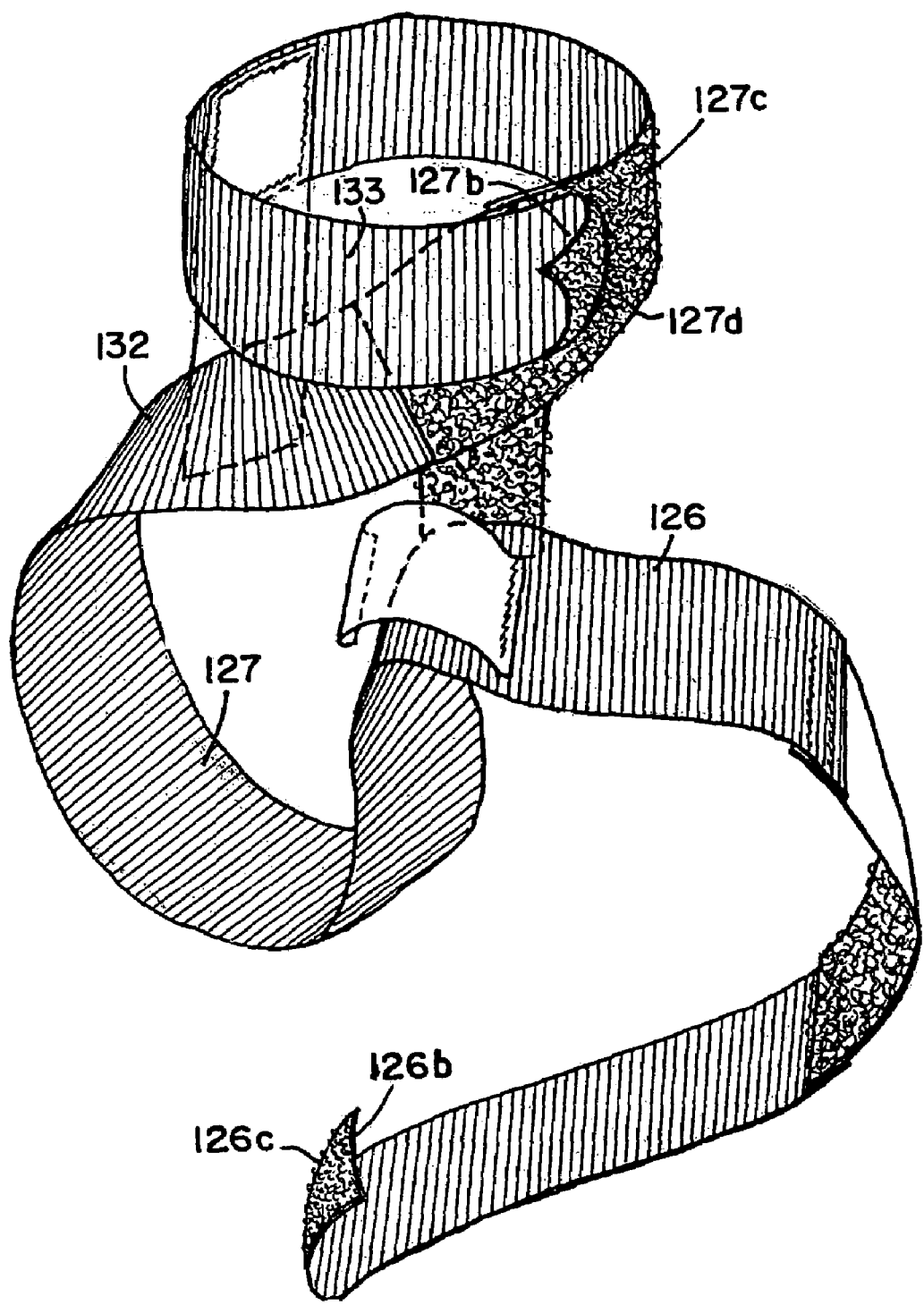
FIG. 12 is a perspective view of the strap segments of the ankle brace shown in FIG. 8, with one of the segments unwrapped.

In viewing FIG. 12, the layout of the hook material 126c, loop material 126d, hook material 127c and loop material 127d can be seen. The layout is similar to that shown in FIG. 6 and will not be described further, it being understood that the layout is the same as that described with respect to FIG. 6.

The strap segments 126, 127 may be made of any suitable material such as a webbing material that is not stretchable. However, there may be some advantage to having a portion of the strap segments 126, 127 that are proximate the ends 126b, 127b to be made of an elastic material to allow for some minimal stretch of an additional one to two inches. This would typically be the portion having the loop materials 126d, 127d.

Figure 10:
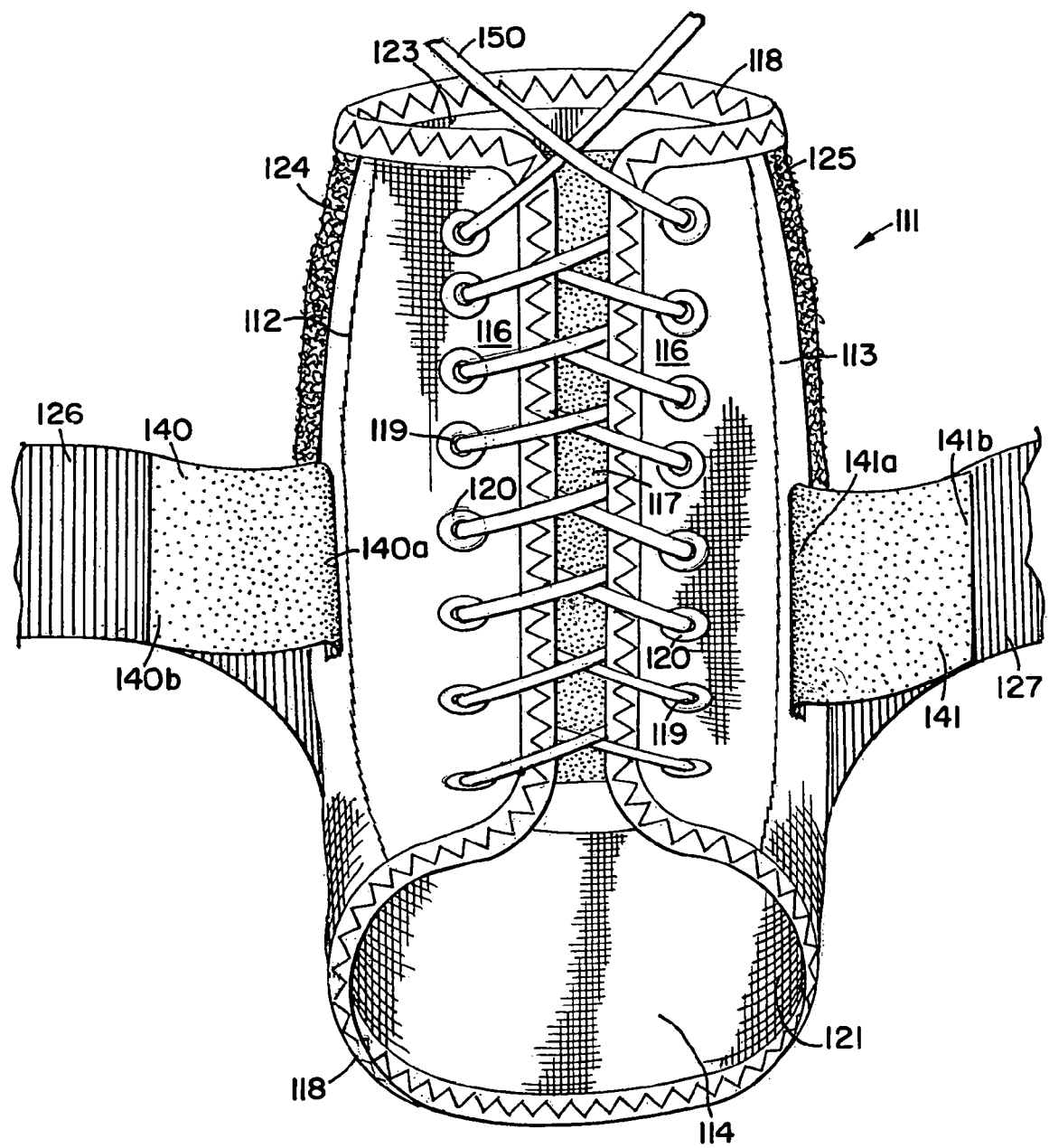
FIG. 10 is a front elevational view of the brace shown in FIG. 7, with the strap segments unwrapped.
Figure 11:
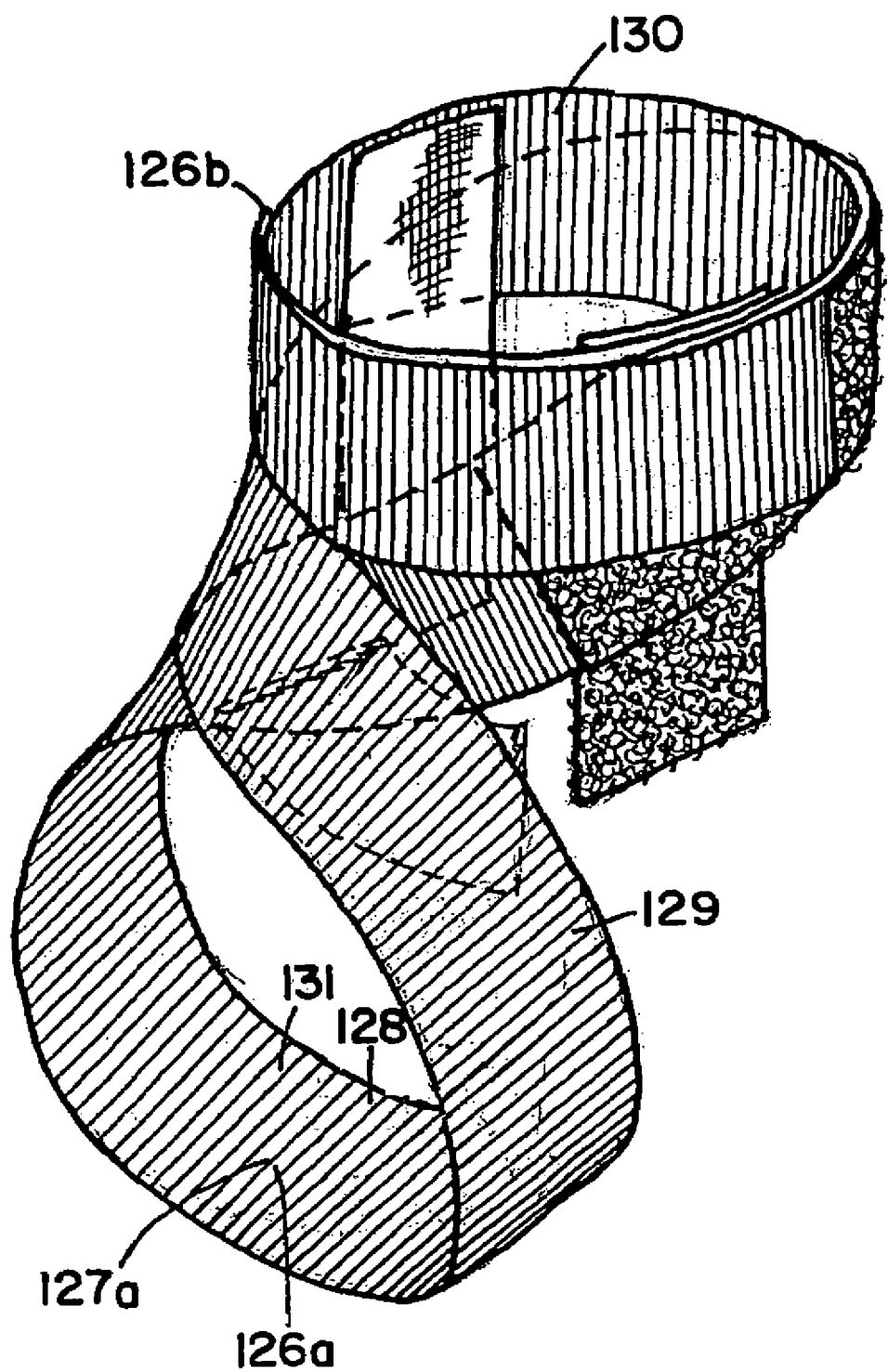
FIG. 11 is a perspective view of the strap segments of the ankle brace shown in FIG. 8.

As shown in FIG. 10, the ankle brace 110 has two prepositioning members 140, 141. The prepositioning members 140, 141 have a first end 140a, 141a that is secured to the first portion 111 by suitable means such as stitching. A second end 140b, 141b is secured to the strap segments 126, 127. The prepositioning members 140, 141 assist in keeping the strap segments 126, 127 in proper orientation as the user is putting on the ankle brace 110. The prepositioning members 140, 141 may have some stretch.

In use, the ankle brace 110 is placed on the user's foot and the laces 150 are tightened. Then, either of the strap segments 126, 127 are tightened first. Similar to the first ankle brace 10, either strap segments 126 or 127 may be tightened first. FIG. 12 shows the ankle brace 110 with the second strap segment 127 secured first. The second strap segment 127 has a first region 131 that is positioned proximate underneath the bottom portion 114 of the first portion 111. Then, the second region 132 of the strap 127 is brought up the right side 112 and across the front portion 116 and the third region 133 is wrapped around the user's ankle and the second end 127b is secured by use of the loop material 127d being secured to the hook material 127c. As previously discussed, it would not be necessary that the strap segment 127 be so long as to encircle the ankle of the user. It would be possible to have the second end 127b terminate earlier and be connected to the body at another point such as proximate the hook material 125. If that is the case, the loop material 127d could be secured to the hook material 125, thereby securing the second strap segment 127. However, as previously stated, it is preferable that the second strap segment 127 extend around and encircle the ankle. Then, the first strap segment 126 is secured. This is shown completed in FIG. 11. The first region 128 is positioned under the bottom portion 114 of the first portion 111. Then, the second region 129 extends up the left side 113 and across the front portion 116. The second region 129 extends across a portion of the second region 132 of the second strap segment 127. The second end 126b is wrapped around the back of the body 111 so that the third region 113 encircles the user's ankle. The strap 126 is secured to itself by means of the hook material 126c mating with the loop material 126d at the second end 126b. The first strap segment 126 also overlaps the second strap 127 at the third region 133 and therefore not only secures itself (strap segment 126) to the first portion 111 but also further secures the second strap segment 127 to the first portion 111. The same discussion with respect to "securing" the strap segments 26, 27 to the body 11 is also applicable to the strap segments 126, 127 being secured to the body 111.

Figure 13:
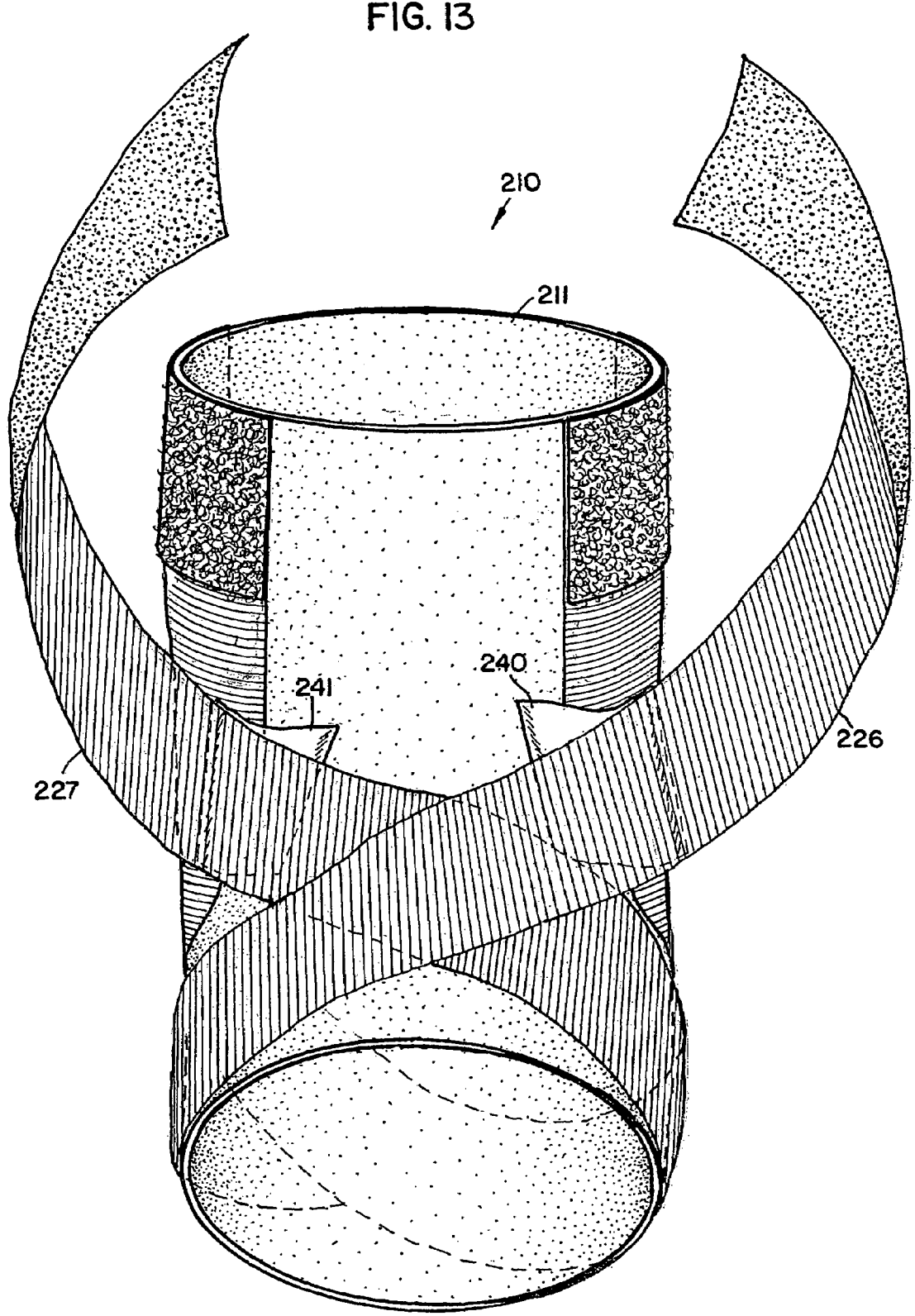
FIG. 13 is a perspective view of another embodiment of an ankle brace in accordance with the present invention.
Figure 14:
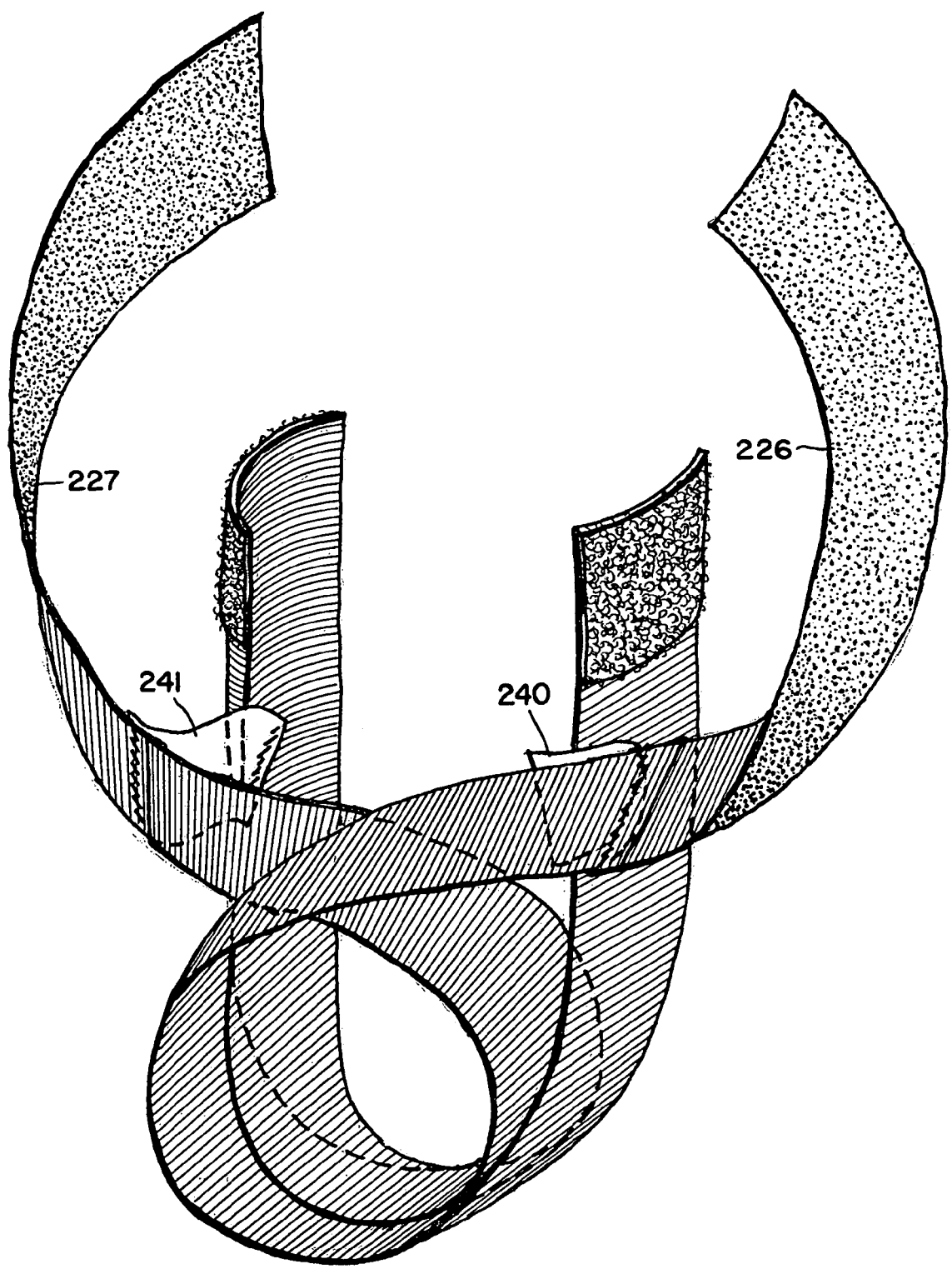
FIG. 14 is a perspective view of the strap segments of the ankle brace shown in FIG. 13.

Referring now to FIGS. 13 and 14, there is another embodiment of the present invention shown. The ankle brace 210 includes a sleeve 211 that is made from a suitable material such as Neoprene. By utilizing a sleeve 211 instead of a boot-like member 11 in the prior embodiment, it is not necessary to utilize laces as the sleeve 211 is simply slipped over the foot of the user. Such a construction is well-known in the art. Further, the ankle brace 210 has a first strap 226 and a second strap 227. The configuration of the straps 226 and 227 is similar to that of straps 26 and 27 and will not be described in more detail. The ankle brace 210 is different from the first embodiment in that it utilizes a sleeve 211 instead of a boot-like member and further the prepositioning members 241 and 240 are positioned in a different location. The prepositioning member 40, in the first embodiment, is attached on the same side as the strap 26 before it crosses over the center line of the front of the brace 10. In the embodiment shown in FIGS. 13 and 14, the prepositioning member 240 is attached after the center line of the front portion of the sleeve 211 after the strap 226 has crossed over. Similarly, the prepositioning member 241 is positioned across the center line after the strap 227 has crossed over the front of the brace 210. Therefore, the prepositioning members 240 and 241 serve to preposition the straps 226 and 227 after they have already crossed the front portion of the brace 210. This embodiment of the brace 210 is simply to show that the prepositioning members 240 and 241 can be positioned on either side of the center line of the front portion of the brace. Further, it is understood that the strap configuration of the second embodiment could also be incorporated with the prepositioning members in the positions as shown in the embodiment in FIGS. 13 and 14.

The operation and tightening of the straps 226 and 227 is similar to that of straps 26 and 27 and will not be described again.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An ankle brace for use in supporting an ankle bone and ankle joint, comprising:
   (a) a body adapted and configured to embrace a user's ankle, the body having a bottom portion for being positioned under a user's foot, a front portion, a back portion, a first side and a second side;
   (b) a first strap having a first end and a second end, the second end secured to the first side, the first strap having a first strap segment having a first region positioned proximate the bottom portion of the body, a second region, proximate the first region, extending up the first side of the body and across the front portion and a third region, between the second region and the first strap's first end, secured to the body and the first end is proximate the third region, the first strap, proximate its second end is aligned to extend down the first side, wherein its first end is releaseably secured to the brace after being wrapped about a user's ankle; and
   (c) a second strap having a first end and a second end, the second end secured to the second side, the second strap having a second strap segment having a first region positioned proximate the bottom portion of the body, a second region proximate the first region extending up the second side of the body and across the front portion, crossing the second region of the first strap segment, and a third region extending around the back of the body, the third region between the second region and the second strap's first end and the first end is proximate the third region, the second strap, proximate its second end is aligned to extend down the second side, wherein its first end is releaseably secured to the brace after being wrapped about a user's ankle.

2. The ankle brace of claim 1, wherein the third region of the first strap segment extends around the back of the body.

3. The ankle brace of claim 1, further comprising the third region of the first strap having a sufficient length to wrap around a user and overlap itself.

4. The ankle brace of claim 3, further comprising the third region of the second strap segment having a sufficient length to wrap around a user and overlap itself.

5. The ankle brace of claim 4, wherein the third region of the second strap segment is secured to both itself and the third region of the first strap.

6. The ankle brace of claim 3, further comprising a first set of hook and loop materials operatively connected to the body and first strap segment, wherein the first strap segment is secured about the body.

7. The ankle brace of claim 6, further comprising a second set of hook and loop materials operatively connected to the body and the second strap segment, wherein the second strap segment is secured about the body.

8. The ankle brace of claim 1, further comprising the first strap segment having a terminal region extending from the first region of the first strap segment and operatively connected to the second side of the body.

9. The ankle brace of claim 8, further comprising the second strap segment having a terminal region extending from the first region of the second strap segment and operatively connected to the first side of the body.

10. The ankle brace of claim 1, further comprising a first prepositioning member having a first end operatively connected to the body and a second end operatively connected to the second region of the first strap segment.

11. The ankle brace of claim 10, further comprising a second prepositioning member having a first end operatively connected to the body and a second end operatively connected to the second region of the second strap segment.

12. The ankle brace of claim 10, wherein the first end of the first prepositioning member is operatively connected to the body and the first strap segment before the first strap segment extends across the front portion.

13. The ankle brace of claim 10, wherein the first end of the first prepositioning member is operatively connected to the body and the first strap segment after the first strap segment extends across the front portion.

14. A method of wrapping first and second strap segments of an ankle brace around an ankle bone and ankle joint, comprising:
  (a) wrapping a first strap segment underneath a bottom portion of a brace before going across a front portion;
  (b) bringing the first strap segment up from the bottom portion and bringing the first strap segment across a front portion of the brace;
  (c) operatively securing the first strap segment to the brace;
  (d) wrapping a second strap segment underneath a bottom portion of a brace before going across a front portion;
  (e) bringing the second strap segment up from the bottom portion and bringing the first strap segment across a front portion of the brace; and
  (f) operatively securing the second strap segment about the brace.

15. The method of claim 14, further comprising:
  (a) wrapping the first strap segment around a back portion of the brace after crossing the front portion; and
  (b) wrapping the second strap segment around a back portion of the brace after crossing the front portion.

16. An ankle brace for use in supporting an ankle bone and ankle joint, comprising:
  (a) a body adapted and configured to embrace a user's ankle, the body having a bottom portion for being positioned under a user's foot, a front portion, a back portion, a first side and a second side;
  (b) a single strap having a first strap segment operatively connected to a second strap segment, the segments operatively connected proximate the bottom portion;
  (c) the first strap segment having a first region proximate the bottom portion of the body, a second region, proximate the first region, extending up the first side of the body and across the second portion and a third region, proximate the second region, secured to the body and a first end, proximate the third region, wherein the first end is releaseably secured to the brace after being wrapped about a user's ankle;
  (d) a second strap segment having a first region positioned proximate the bottom portion of the body, a second region, proximate the first region, extending up the second side of the body and across the front portion, crossing the second region of the first strap segment, and a third region extending around the back of the body, the third region proximate the second region, and a second end, proximate the third region, wherein the second end is releaseably secured to the brace after being wrapped about a user's ankle; and
  (e) the single strap operatively connected to the body wherein the first regions are positioned under the bottom portion.

17. The ankle brace of claim 16, wherein the third region of the first strap segment extends around the back of the body.

18. The ankle brace of claim 16, further comprising the third region of the first strap having a sufficient length to wrap around a user and overlap itself.

19. The ankle brace of claim 16, further comprising a first prepositioning member having a first end operatively connected to the body and a second end operatively connected to the second region of the first strap segment.

20. The ankle brace of claim 19, further comprising a second prepositioning member having a first end operatively connected to the body and a second end operatively connected to the second region of the second strap segment.

21. The ankle brace of claim 19, wherein the first end of the first prepositioning member is operatively connected to the body and the first strap segment before the first strap segment extends across the front portion.

22. The ankle brace of claim 19, wherein the first end of the first prepositioning member is operatively connected to the body and the first strap segment after the first strap segment extends across the front portion.

* * * * *